US006251592B1

(12) United States Patent
Tang et al.

(10) Patent No.: US 6,251,592 B1
(45) Date of Patent: Jun. 26, 2001

(54) STR MARKER SYSTEM FOR DNA FINGERPRINTING

(75) Inventors: JianQing Tang, Brossard; Serge B. Melançon, Outremont, both of (CA)

(73) Assignee: Procrea BioSciences Inc., Montreal (CA)

( * ) Notice: Subject to any disclaimer, the term of this patent is extended or adjusted under 35 U.S.C. 154(b) by 0 days.

(21) Appl. No.: 09/084,120

(22) Filed: May 26, 1998

(51) Int. Cl.[7] .............................. C12Q 1/68; C12P 19/34; C07H 21/04
(52) U.S. Cl. .......................... 435/6; 435/91.2; 536/23.1; 536/24.3
(58) Field of Search .................... 435/6, 91.2; 536/24.3, 536/23.1

(56) References Cited

U.S. PATENT DOCUMENTS 5,576,180    11/1996    Melançon et al. .................. 435/6

OTHER PUBLICATIONS

Busque et al., J. of Forensic Sciences, vol. 42, pp 1147–1153, 1997.*

Tang J.Q., et al., *Mammalian Genome* 6:345–349, 1995.

* cited by examiner

*Primary Examiner*—Lisa B. Arthur
*Assistant Examiner*—Jehanne Souaya
(74) *Attorney, Agent, or Firm*—Swabey Ogilvy Renault; Christian Cawthorn

(57) ABSTRACT

The present invention relates to novel STR markers for DNA fingerprinting. More specifically, the invention relates to seven different STR markers for DNA fingerprinting of a DNA sample, whereby each marker comprises a sequence selected from the group consisting of SEQ ID NOS:1 to 7 as set forth in FIGS. 1A–1B.

13 Claims, 4 Drawing Sheets

Sequence 1: Sextolet 900

| | | | | | |
|---|---|---|---|---|---|
|AAAGGCAGGA|TAAATGTTTG|ACTTTTTTCC|TTTTATTTGC|CACTTTTCAA|AACAAGTATC  60|
|ATAATAAACT|CACTAATTTA|AACATTTTGA|TGTATTTTAA|TACAGGGTAG|TTATTGTTCT 120|
|TATTGATGCT|TAAATTATCC|ATCTTTGACC|AATGGGAGCC|TAGTTATTTT|GGTTCCCTTG 180|
|ACATTTTGAC|AGAAATCCAA|CGATCTTTCG|ATCAATGTTT|GGTAGTTTCC|TTGTTTCTAG 240|
|TTTATTTTGT|ACTTTTTCTT|CTCCTGGTTT|TAGAATTAGC|CTTTTTCCTA|AGGATACTCA 300|
|GTTTTTTTTT|TTGACACAGT|TATACATGAT|GTTTTATAGG|TTAACTATGA|TAGAAAAAGC 360|
|CTTGATAGGC|TTCTTTGTTA|GAAAGGAAAG|GCCAAATATT|TCCAGGAATA|TTGGAGGTTC 420|
|AGTTCCTTGG|CACAGATAGG|TGGTTTTCTC|TGAAATTAAT|TTGGAAAATT|CTATCAGGTG 480|
|AGAGCATATC|ATTGTTGTGT|TTGTAAAAAA|CAATGGCCAA|TAGAGATAAC|AGTTTATGAA 540|
|AAACCACTGT|TTTCTATAAT|GAAGAAGAAG|ACATCTTATC|TTTGTAAACA|AAGGAGCAAA 600|
|GGAAAGTGTG|ATTTCAGAAC|TGCTTGGTTC|TATGTACTGG|AGATTCAGAT|GTGGGAGGC 660|
|ACTCAGAAGT|GTGACTTTTG|GTCTCAGCCC|TGTTTGGAGC|CCTTAGCCCT|AAGTCAGAGA 720|
|ATGTACACAA|TCTACCTGGG|GAGGCTGAGC|TGCCCACTGG|GAACAGAGGT|TCTTGGGTGT 780|
|TCCACTGCTC|CCAAGTCAGA|ATCCTGGGTC|TCCTACTAAT|ACCTGGGCAG|TTCACTTTTC 840|
|TCAGGTCTCT|TTTCTTTTCT|AGCAGAGCCT|AGAGCAGAGT|AACTACTTCA|GAATGCGTTT 900|
|TGGATGAAAT|GAGATGACCA|CATGAGACAG|CAACAACTTG|TGCTCAGCTT|GGGCCCCTTC 960|
|TTTCTTTCCT|TTCTCTTTTC|TTTCCTTCTT|TCCTTCTTTA|GAGTCTCGCT|CTG       1013|

(SEQ ID NO:17)

Sequence 2: Sextolet 800

| | | | | | |
|---|---|---|---|---|---|
|TTTCCAGCTG|GAACGAAGAC|CCAGCCACAT|GCCTGCATTC|ACACCTCTTC|CAGTCTCTTT  60|
|CCTTCTTTCT|TTTTCTTTCT|CTTTCCTTCT|TTCCTCCCTT|TCTTTTTTCT|TTCTTTCTTT 120|
|CTGACAGAGT|CTCGCTCTG|| | |           139|

(SEQ ID NO:18)

Sequence 3: Sextolet 700

| | | | | | |
|---|---|---|---|---|---|
|AAGACCCAGC|CACATGCCTG|CATTGACATA|CACATAAGCA|GTCACCAAGA|CACAATCCAA  60|
|CTGCAGCAGT|GATCAACAAG|CCCCAAGAGT|GACCAGACTG|AGTCAGGGTG|CTTTCCTCTC 120|
|TCAGCTGCTT|GGCTTGTTCA|ATCTCAAATG|GAAATTCCTT|CAGAATTCCC|CAAATCAAGA 180|
|GGAGCGGTTC|CTGCTTTTTG|GACTCACAGA|AGACACTCAC|TTGTCCAGAT|GCAGATGTGC 240|
|ACATACAGAC|ACAAATAAGC|AATTATTAAC|AAGCCTCAAG|AGTGTCCAAA|CTGAGACAGG 300|
|GAGCTTTCCT|CTCTTCATTG|GTTAGGCTTG|TCAACCTGC|AAATAGATTC|CTCAAATCTA 360|
|GAGGAGCCAT|ATTTGCTGTC|AGCTACCCAC|AAAAGACACT|TATCTGTCCA|GAGACAGACG 420|
|TCAATTTTTT|CTTTCTTCCT|TTTCTTTCTT|CTTTCTCTTT|CTTCTTTCTT|TTTTTTTTTT 480|
|TTTTTGACAG|AGTCTCGCTC|TG|| |        502|

(SEQ ID NO:19)

Fig. 1A

Sequence 4: Sextolet 180

```
TTTGTTTCTA AGCATTTGTG TTTATAAATG AATACATGTA AAATATATTT TTGCTTCTTA   60
ATTTATGGAC TATCTTCTGA TTTCCCTTCA TTTTTTAATA GCTGTTTTTA ACCTGAGAAT  120
TCTATCTAGC CCAACTGAAA TTATTACTTG TTTTATTTTA TGTATTTGTT TATTTGAGAT  180
AGAGTCTCGC TCTGA                                                   195
                                                        (SEQ ID NO:20)
```

Sequence 5 : Sextolet 150

```
TCTAAAGTAC TTATCAGAAA CATTTGTTTC TTTTTAAAAA AAAATTTTTG TTTCTTTTTT   60
AAAAAAATAT TTTGTATTGT TTAGTTTTTG CAGAGATGGA CGGTCATCAT GTTTGTTTG  120
AGAGTCTCGC TCTG                                                    134
                                                        (SEQ ID NO:21)
```

Sequence 6: Sextolet 110

```
AGCCACATGC CTGCATTCAC AAGTAAGAAG GAAAAGCCTC TTGGGAAAGT AAGTCTTTGT   60
TTTTATTGGT TTTTGTTTTG CACAGAAGCC ACGTAAATCC ACCATCCTAA ATAA         114
                                                        (SEQ ID NO:22)
```

Sequence 7: Sextolet 100

```
CAGAGCGAGA CTCTGTCAAT AAATAAACAA ACAAAAACTC TGGTTCCTGG CGGCTTCTCT   60
TGAAATATCA GAATGGTACC ACTGGGTAAC C                                   91
                                                        (SEQ ID NO:23)
```

Fig. 1B

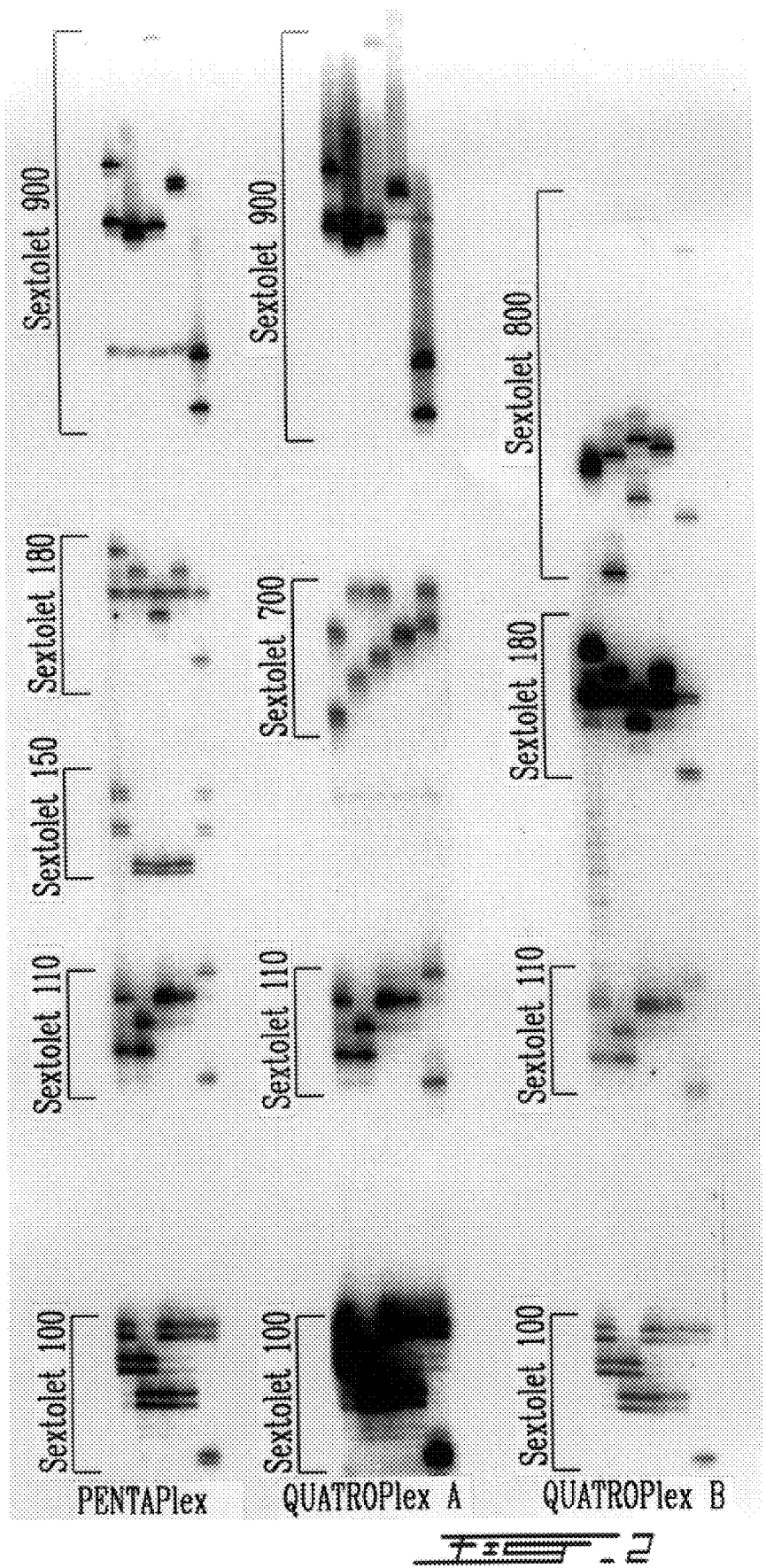

STR MARKER SYSTEM FOR DNA FINGERPRINTING

BACKGROUND OF THE INVENTION (a) Field of the Invention

The invention relates to seven novel STR markers for DNA fingerprinting.

(b) Description of Prior Art

Creating a reliable, informative system for human identification has been long envisaged in forensic science. Polymorphism at the DNA level provides information regarding the segregation pattern of parental chromosomes during the mating process and hence discloses a person's genetic identity and thus, becomes a powerful tool for DNA fingerprinting. The information extracted from a specific DNA marker can be measured by the frequencies of each allele, and its heterozigosity and matching probability in a population. When several markers are being used together in a fingerprinting procedure, the global informativeness of the system depends on the informativeness extracted from each individual marker. Higher informativeness can only be obtained if more markers or more informative markers are used.

The Southern blot technique has been used to analyze restriction fragment length polymorphism (RFLP), a highly informative system which, however, requires considerable amounts of DNA and long periods of time to obtain, analyze and interpret the results.

The Polymerase chain reaction (PCR) has been widely used since the late 80s and proved to be a highly efficient and sensitive method to disclose and analyze DNA polymorphism. Most markers having been so far analyzed by PCR are of STR (Short Tandem Repeats) polymorphism. In a STR marker, the polymorphism arises from the number of repeats of short stretches of DNA. The number of repeats varies between individuals in the general population and thus provides a source for human identification at the DNA level. Ordinary PCR analyzes one marker at a time. More recently, primers were pooled and multiple markers were amplified in one PCR reaction. Since optimized multiplex PCR consumes considerably less reagent and time for same quality results, it greatly improves DNA fingerprinting procedures. The STR markers analyzed using multiplex PCR techniques proved to be fast, reliable and cost effective.

Markers and multiplex systems have been formulated by different suppliers for DNA forensic studies or paternity testing. The matching probabilities of individual systems reach a level of 1 in $1 \times 10^8 - 10^9$. These multiplex systems combine the same 8 to 9 markers with one or two markers differing from one system to another. The need for a unique, independent and highly informative marker system was overdue. Its availability will not only strengthen the existing DNA forensic/paternity testing services, but also provide an independent counter-expertise often required in various situations.

SUMMARY OF THE INVENTION

In accordance with the present invention, we have recently invented a PCR system that fulfills these requirements. This multiplex PCR system analyzes seven markers located on 6 different human chromosomes. Two markers, Sextolet 900 and Sextolet 100 have been reported previously and greatly improved in their present forms. Five additional markers, Sextolet 110, Sextolet 150, Sextolet 180, Sextolet 700 and Sextolet 800 have been discovered and analyzed. Optional multiplex PCRs amplify diverse combinations of these seven markers. The system has been made suitable for different levels of laboratory equipment. The conventional radio-labeled multiplex PCR procedure can be used in routine genetic diagnostic laboratories where a DNA sequencer is not available. The fluorescent-dye labeled multiplex PCR procedure improves the convenience of manipulation, allows for automation and considerably accelerates the output. Data from a population study have yielded a matching probability in the $10^{10}$ scale with the seven markers, and a typical paternity index of over 4250.

In accordance with the present invention there is provided a STR marker system for DNA fingerprinting of a sample DNA, which comprises a sequence selected from the group consisting of SEQ ID NOS:1 to 7 as set forth in FIGS. 1A–1B and complementary sequences thereto.

The DNA is from a human patient, such as a foetus, embryo, newborn, children, adult, live or deceased for identification thereof.

In accordance with the present invention there is provided the use of the STR marker system of the present invention to design primers to amplify the marker.

In accordance with the present invention there is provided a DNA amplification primer pair for the simultaneous amplification of at least one STR marker, which comprises a pair of 5' and 3' primers selected from the group consisting of:

| 5' Primer (5'–3') | 3' primer (5'–3') |
|---|---|
| CAGAGCGAGACTCT (SEQ ID NO:5) | GCCGGGCGCCCAAGAGAAGCCGCCAGGAAC (SEQ ID NO:8) |
| GGCCGCCGGAAAAGCCTCTTGGGAAAGTA (SEQ ID NO:6) | CCGCCGCGCATTTAGGATGGTGGATTTAC (SEQ ID NO:9) |
| CAGAGCGAGACTCT (SEQ ID NO:5) | GTACTTATCAGAAACATTTGTTTC (SEQ ID NO:10) |
| CAGAGCGAGACTCT (SEQ ID NO:5) | TGCTTCTTAATTTATGGACTATCT (SEQ ID NO:11) |
| CAGAGCGAGACTCT (SEQ ID NO:5) | CCGGCGGCCGGGGCCCTGCTTCTTAATTTATGGACTATCT (SEQ ID NO:12) |
| CAGAGCGAGACTCTGTCA (SEQ ID NO:7) | ATCTGTCCAGAGACAGACGTCAAT (SEQ ID NO:13) |
| CAGAGCGAGACTCTGTCA (SEQ ID NO:7) | GCCTCAAGAGTGTCCAAACTGAGAC (SEQ ID NO:14) |
| CAGAGCGAGACTCTGTCA (SEQ ID NO:7) | CGGCCGGGGCCCATGCCTGCATTCACACCTCTTCCAGT (SEQ ID NO:15) |

-continued

| 5' Primer (5'–3') | 3' primer (5'–3') |
|---|---|
| CAGAGCGAGACTCT (SEQ ID NO:5) | ATGCGTTTTGGATGAAATGAGATG (SEQ ID NO:16) |

In accordance with the present invention there is provided a method for the DNA fingerprinting identification of genetically related or unrelated individuals, which comprises the steps of:

a) collecting genomic DNA sample of the individuals;

b) performing DNA amplification of the DNA samples of step a) using at least two primers for the amplification of at least one marker or a primer pair of the present invention; and c) separating the amplified DNA segments of step b);

whereby seven markers of the genomic DNA of different size are amplified and serve as DNA finger-printing of the individuals.

The DNA amplification of step b) may be effected by PCR or by asymmetric PCR procedure.

The DNA separation of step c) may be effected using an automated genetic analyzer or a gel electrophoresis procedure.

The gel electrophoresis procedure may be a urea-PAG separation method.

In accordance with the present invention there is provided a method for the DNA fingerprinting identification of human DNA samples, which comprises the steps of:

a) performing DNA amplification of the DNA samples using at least two primers for the amplification of at least one marker or a primer pair of the present invention; and b) separating the amplified DNA segments of step a);

whereby seven markers of the genomic DNA of different size are amplified and serve as DNA finger-printing of the DNA samples.

The DNA finger-printing of the DNA samples may be for verifying transplanted tissues in research or therapeutic procedures; for single cell genetic profiling in research or therapeutic procedure; for verifying sample mix-up or contamination; or for testing, establishing or verifying paternity, maternity or consanguinity of individuals.

In accordance with the present invention there is provided a kit for simultaneous amplification of STR markers, which comprises:

a) the primer pairs listed above; and b) typed DNA sequences of the present invention.

The kit may further comprise c) the typed DNA sequences of all alleles of the seven markers.

BRIEF DESCRIPTION OF THE DRAWINGS

FIGS. 1A–1B illustrate the complete sequence of all seven STR marker (SEQ ID NOS:17–23);

FIG. 2 illustrates the results of the auto-radiographs for different combinations of the seven markers for three multiplex PCRs.

DETAILED DESCRIPTION OF THE INVENTION

Figure 3A:
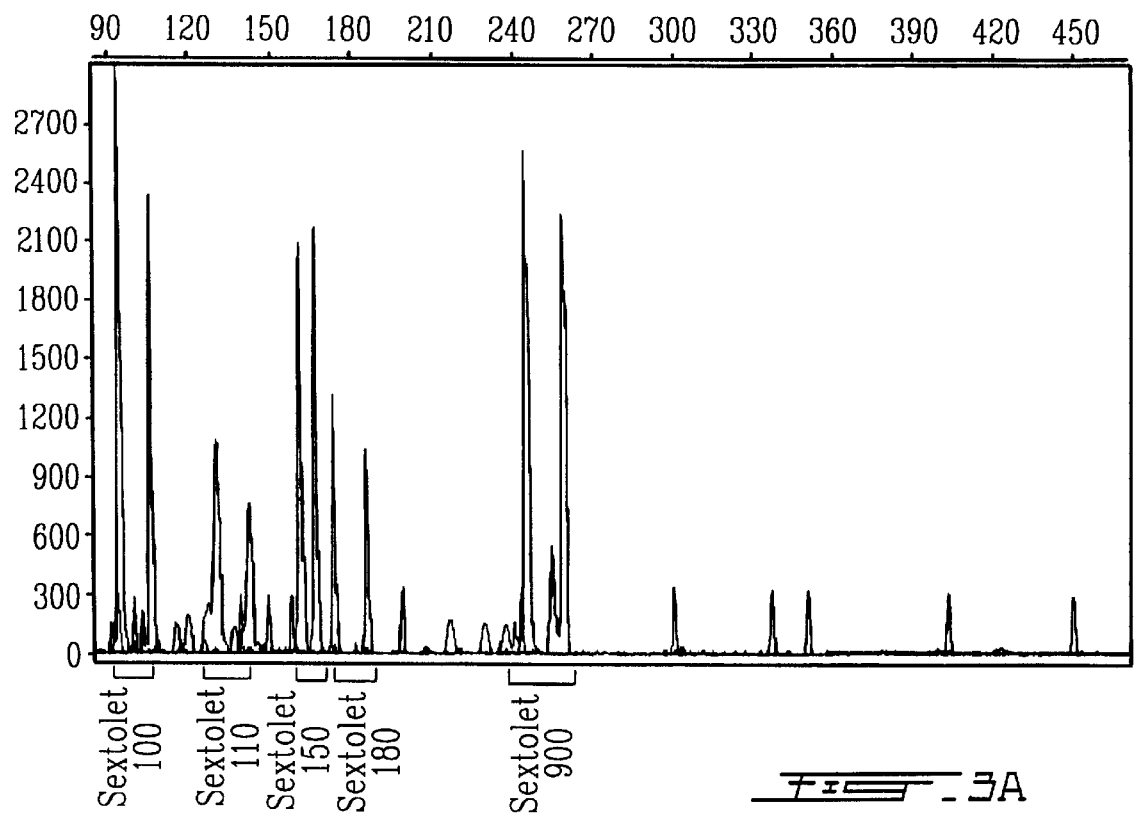
FIGS. 3A–3B illustrate the results of the fluorescent-dye labeled markers analyzed by GA310 (3A, top: M1; bottom: M2. 3B, top: M1+M2; bottom: M3).
Figure 3B:
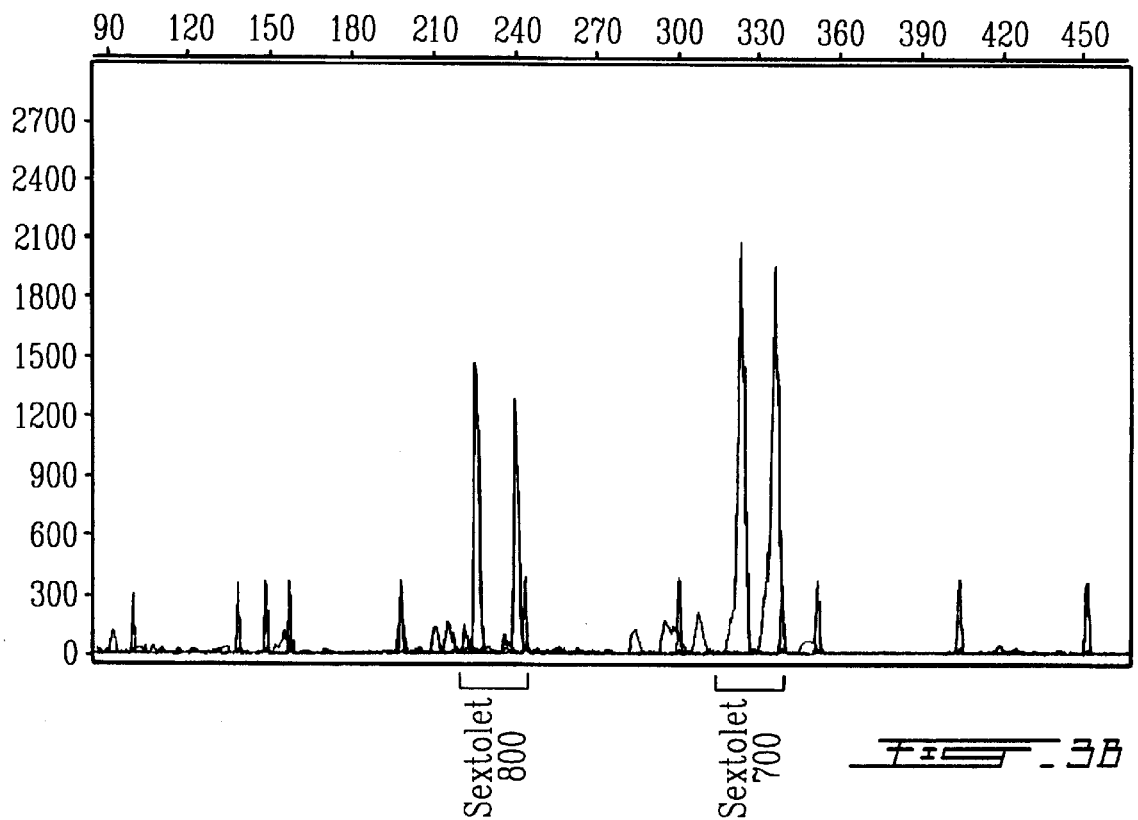

The present invention provides a system of multiple DNA markers for human identification. The multiple markers included in this invention are firstly amplified by multiplex PCRs using either radio-labeled or fluorescent-dye labeled unique primers. PCR products are separated according to their size. The separation is best achieved using either polyacrylamide gel electrophoresis or capillary electrophoresis with an automatic Genetic Analyzers™. The present invention describes markers which have high discrimination power and matching probability.

The matching probability of all seven markers together is at the level of one in $10^{10}$ individuals, i.e., twice the present human population of the world. Human identification using this new system is more informative than using any DNA profiling system currently available. Using this new system, a typical paternity test will require less than 24 hours of laboratory processing time and yield a mean paternity probability of 99.98%.

The Markers in Accordance With the Present Invention

Previous study have revealed that multiple markers can be amplified using one pair of primers. However, this strategy usually generates high background and unsatisfactory resolution of all the individual markers (Tang J.Q., et al., *Mammalian Genome* 6:345–349, 1995). The new strategy of the present invention uses the shared 5' primers in combination with specific 3' primers. Each 3' primer is designed independently so the size of the corresponding marker can be adjusted and the background amplification can be reduced as much as possible. Seven markers were accordingly designed in accordance with the present invention (Table 1).

TABLE 1

| | | The markers | | | | |
|---|---|---|---|---|---|---|
| Markers | H | STR | Chr. Loc. | Base pair | O-allele | E-allele | Indiv. |
| Sextolet 100 | 0.765 | AAT | 5q31.2–33.2 | 88 to 118 | 10 | 11 | 723 |
| Sextolet 110 | 0.768 | AAT | 7p12.3–13 | 127 to 148 | 8 | 8 | 594 |
| Sextolet 150 | 0.662 | AAAAC (SEQ ID NO:1) | 1p11.2–1q12 | 155 to 180 | 6 | 6 | 668 |
| Sextolet 180 | 0.726 | ACAT | 2q14.1–14.3 | 165 to 193 | 10 | 12 | 549 |

TABLE 1-continued

The markers

| Markers | H | STR | Chr. Loc. | Base pair | O-allele | E-allele | Indiv. |
|---|---|---|---|---|---|---|---|
| Sextolet 700 | 0.925 | (AAAG)(GAAG)(AAAG) (SEQ ID NO:2) | 5q22.2–23.1 | 305 to 380 | 42 | 76 | 429 |
| Sextolet 800 | 0.934 | (AAAG)(AG)(AAAG) (SEQ ID NO:3) | 10p11.23–12.2 | 196 to 291 | 54 | 96 | 435 |
| Sextolet 900 | 0.967 | (AAAG)(AG)(AAAGG) (SEQ ID NO:4) | 18q11.2–21.2 | 233 to 399 | 109 | 166 | 427 |

H: Heterozigosity
STR: Short Tandem Repeat
Chr. Loc.: chromosome locations
Base pair: length of the markers in base pair based on the primers described in the M1 and M2 sets of primers of this invention. However, the lengths may change when different specific primers are used or when the length of specific primers is changed by any means of nucleotide additions.
O-allele: number of alleles observed
E-allele: number of expected alleles in the general population
Indiv.: number of individuals analyzed As established from the allele segregation data among large families, chromosomal locations of the seven markers showed in Table 1 were on different chromosomes, with the exception of Sextolet 100 and Sextolet 700 being 26 cM apart on chromosome 5. For applications requiring that none of the markers be linked at all, only Sextolet 700 will be used for calculation. For applications tolerating some degrees of linkage, both markers may be used for calculation.

Amplification of these markers requires a total of 10 primers. Specific 3' primers were designed for each of the seven marker. A specific 5' primer is required for Sextolet 110, a non-specific primer is shared by Sextolet 800 and 700. The Sextolet 100, Sextolet 150, Sextolet 180 and Sextolet 900 also share one 5' primer, Trio-5' (R14B/264 in U.S. Pat. No. 5,576,180). The sequences of the primers are listed in Table 2.

Two markers, Sextolet 100 and Sextolet 900, have been derived from Q120 and Q900, respectively (Tang J.Q., et al., *Mammalian Genome* 6:345–349, 1995). In accordance with the present invention, however, the procedures and the primers needed to reveal Sextolet 100 and Sextolet 900 differ from markers Q 120 and Q 900, in this invention. Markers Q120 and Q900 were described in U.S. Pat. No. 5,576,180. Marker Sextolet 900 was the subject of another US patent application (pending) by our group. These markers have been modified and further optimized to be included in the current protocol. Significant improvement to these markers has been achieved. More efficient amplification, lower background and desirable fragment sizes were achieved in accordance with the present invention.

A choice of two primers has been made accessible for Sextolet 100. Either one combined with Trio-5', can amplify Sextolet 100 with comparable quality, as compared to Q120. The desired size of Sextolet 100 amplified by the new primers facilitates the analysis of the multiplex PCR.

The major modification of the Sextolet 900 (Q900 in U.S. Pat. No. 5,576,180) has been described in the patent application (patent pending) related to this invention. Briefly, a non-polymorphic sequence adjacent to the polymorphic STR region was uncovered. Several primers were designed and tested most of them proved to be good to amplify the Sextolet 900. The best primer to amplify Sextolet 900, Sextolet 900E, was selected in accordance with this invention. Depending on the alleles amplified, the Sextolet 900E amplifies this marker at sizes of base pair ranging from 233 to 399 with minimal background.

Sextolet 110, Sextolet 150, Sextolet 180, Sextolet 700 and Sextolet 800 are newly discovered STR markers. They were

TABLE 2

The primers for each markers

| Marker | 5' Primer (5'-3') | 3' primer (5'-3') |
|---|---|---|
| 100C | CAGAGCGAGACTCT (SEQ ID NO:5) | GCCGGGCGCCCAAGAGAAGCCGCCAGGAAC (SEQ ID NO:8) |
| 110Bs | GGCCGCCGGAAAAGCCTCTTGGGAAAGTA (SEQ ID NO:6) | CCGCCGCGCATTTAGGATGGTGGATTTAC (SEQ ID NO:9) |
| 150 | CAGAGCGAGACTCT (SEQ ID NO:5) | GTACTTATCAGAAACATTTGTTTC (SEQ ID NO:10) |
| 180A | CAGAGCGAGACTCT (SEQ ID NO:5) | TGCTTCTTAATTTATGGACTATCT (SEQ ID NO:11) |
| 180F | CAGAGCGAGACTCT (SEQ ID NO:5) | CCGGCGGCCGGGGCCCTGCTTCTTAATTTATGGACTATCT (SEQ ID NO:12) |
| 700B | CAGAGCGAGACTCTGTCA (SEQ ID NO:7) | ATCTGTCCAGAGACAGACGTCAAT (SEQ ID NO:13) |
| 700E | CAGAGCGAGACTCTGTCA (SEQ ID NO:7) | GCCTCAAGAGTGTCCMACTGAGAC (SEQ ID NO:14) |
| 800G | CAGAGCGAGACTCTGTCA (SEQ ID NO:7) | CGGCCGGGGCCCATGCCTGCATTCACACCTCTTCCAGT (SEQ ID NO:15) |
| 900E | CAGAGCGAGACTCT (SEQ ID NO:5) | ATGCGTTTTGGATGAAATGAGATG (SEQ ID NO:16) | either cloned from a STR marker enriched library or from simultaneously amplified multiple markers. These markers were firstly cloned and then entirely sequenced (FIGS. 1A and 1B). Various primers were designed from non-polymorphic stretches of each marker. Optimal primers were chosen and amplification conditions were selected and conditions for individual as well as for multiplex amplifications of the markers were set.

Simple STR with tri-, tetra- or penta-repeated units were identified in Sextolet 100, Sextolet 180 and Sextolet 150, respectively. For result analysis, an ordinary PAGE gel migration with a resolution of 3 bp is needed. This resolution scale can be reached using common methods and routine sequencing gel procedures.

Complex STR regions, made of an AG-rich stretch of DNA (about 200 bp) were found in Sextolet 700, Sextolet 800 and Sextolet 900. Their STR regions contain several polymorphic units which allow for a large number of variations between individuals. In reality, the relative combination of each unit may lead to differences of only one base pair between alleles. If we take Sextolet 900 as an example, allele one (1) may consist of a complex STR as $[(AAAG)_{14}(AG)_8(AAAGG)_{15}]$ (SEQ ID NO:4), the length of which is $4 \times 14 + 2 \times 8 + 5 \times 15 = 147$ bp, while allele two (2) may have $[(AAAG)_{13}(AG)_8(AAAGG)_{16}]$ (SEQ ID NO:4), differs by only one base pair with a length of $4 \times 13 + 2 \times 8 + 5 \times 16 = 148$ bp. Similar phenomena were observed with Sextolet 800 and Sextolet 700 markers, due to their complexity.

Therefore, analysis of these markers needs to rely on a separation program at the one-base pair resolution in the 200 to 400 bp range with a constant size reference scale present in each run. Although polyacrylamid sequencing gels are able to resolve one base pair at these sizes, between gel variations and omission of internal size reference standards certainly represent some disadvantages of using PAGE.

The Genetic Analyzer™310 from PE-ABI (Perkin-Elmer-Applied BioSystems) uses a micro-capillary column to separate DNA fragments. Two types of polymers are proposed: POP6 (Performance Optimized Polymer 6) for DNA sequencing applications and POP4 (Performance Optimized Polymer 4) for fragment analysis. We have found that the resolution ability of POP4 was inappropriate for the analysis of Sextolet 900, Sextolet 800 and Sextolet 700. Alleles differing by only one base pair came out as a single wider peak instead of two separate peaks in the high molecular weight range. A new module was created using POP6 for fragment analysis (see below). Using this new module, one base pair resolution at as high as 500 bp was achieved, allowing for complete analysis of Sextolets 900, 800 and 700, with some increment in the migration time (50 min. with POP6 instead of 30 min. with POP4). We have done more than a thousand runs using this module, and both resolution and signal quality have remained steadily reproducible.

Multiplex PCR was designed to accelerate the analysis procedure. Different combinations of the seven markers were tested to reach optimal amplification. With the exception of Sextolet 150 which can not be included in the multiplex PCR with Sextolet 75-5' primer, all combinations were functional. Therefore, two PCRs will be needed to amplify all seven markers. For the following six markers, Sextolet 100, Sextolet 110, Sextolet 180, Sextolet 700, Sextolet 800 and Sextolet 900 a single multiplex reaction is needed. Considering that Sextolet 150 is the least informative of the seven markers, Data will suffice for most applications. The multiplex PCRs using combinations of our seven markers are listed in Table 3 (table 3: multiplex PCR).

TABLE 3

Some multiplex PCRs and their informativeness

| Multiplex PCR | Markers | Primer Labeling | Including Sextolet 100 | | Excluding Sextolet 100 | |
|---|---|---|---|---|---|---|
| | | | Pm | Typical PI | Pm | Typical PI |
| PENTAPlex | 100, 110, 150, 180, 900 | $^{18}P$ | $9.9 \times 10^6$ | 184 | $8.9 \times 10^5$ | 88 |
| QUATROPlex A | 100, 110, 700, 900 | $^{32}P$ | $1.9 \times 10^7$ | 388 | $8.2 \times 10^5$ | 186 |
| QUATROPlex B | 100, 110, 180, 800 | $^{32}P$ | $1.6 \times 10^5$ | 55 | $1.5 \times 10^4$ | 26 |
| M1 | 100, 110, 150, 180, 900 | F | $9.9 \times 10^6$ | 184 | $8.9 \times 10^5$ | 88 |
| M2 | 700, 800 | F | $1.5 \times 10^4$ | 48 | — | — |
| M1 + M2 | 100, 110, 150, 180, 700, 800, 900 | F | $1.5 \times 10^{11}$ | 8870 | $1.4 \times 10^{10}$ | 4255 |
| M3 | 100, 110, 180, 700, 800, 900 | F | $2.5 \times 10^{10}$ | 5453 | $2.3 \times 10^9$ | 2616 |

F: fluorescent-dye labeling
Pm: matching probability

Radio-labeled multiplex PCR products are electrophorized using a sequencing gel. Results are obtained following autoradiography of the dried gel (FIG. 2). Each marker shows up at a predetermined position on the gel, which has been designed following some previous population studies. Allelic fragments of each individual marker are easy to identify as they tend to cluster in definite areas of the gel. In very rare instances, allelic fragment of adjacent markers may overlap. Separate PCRs will be needed to resolve the individual markers.

Fluorescent-labeling multiplex PCR were analyzed using the GA310. The GA310 has the advantage over conventional gel electrophoresis apparatus of being highly automated. Factors affecting gel electrophoresis performance such as temperature, gel filling, sample loading and power level are minimized under the GA310™ computer controlled conditions. As a result, variation between samples is very small. Results are visualized with the computer program GeneScan 2.1™ (PE-ABI). The markers are easy to identify by the different colors of their peaks when using primers labeled with different fluorescent dyes. Reference size standards are included in each migration. The size of each allelic fragment is obtained. Both size and color data are combined to identify each marker alleles. The fluorescent dyes used in this system will remain attached to the primer. The added molecule will change the migration rate of the DNA fragment (peak shift). Since different dyes will be used to identify the markers, we recommend to always use the same dye for the same marker to avoid peak shifting errors.

Method

We use two methods to reveal the Sextolet marker. The first method uses radio-labeled primers in (hot) multiplex PCRs coupled with high resolution polyacrylamide gel electrophoresis (PAGE) to resolve the markers. The second method relies on fluorescent dye-labeled primers in (cold) multiplex PCRs coupled with automatic DNA fragment analysis using a GA310™ computer or the equivalent.

Hot Multiplex PCR

Multiplex PCR

The reaction is carried out in a 200 µl thin wall tube in a Robocycler™ (Stratagene). The reaction mixture (20 µl) includes 20 ng of genomic DNA extracted from from biological sample fluid or dried biological samples (DBS) according to conventional methods as needed. One unit of Taq DNA polymerase or Platinum™ Taq polymerase (GIBCO-BRL), and 0.2 mM each of four dNTPs, in 10 mM Tris-HCl, pH 9.0, 50 mM KCl, 2.0 mM MgCl$_2$, 5% formamide, 1% dimethyl sulfoxide (DMSO), 0.01% gelatin with primers (Table 4). The reaction is carried out with 30 cycles at 94° C. for 45 sec., 52° C. for 60 sec., and 72° C. for 60 sec. All components except labeled primers, the Taq polymerase and DNA sample can be premixed and stored frozen at below −20° C.

Gel Electrophoresis

To the 20 µl of reaction, 10 µl of loading buffer (95% formamide, 0.04% Bromophenol blue, 0.04% Xylene cyanol and 5 mM EDTA) is added. The sample is heated at 94° C. for 5 min. and immediately cooled to 4–6° C. Five to six (5–6) µl of the sample are loaded into a sequencing type gel (6% polyacrylamide:bis-acrylamide 19:1, 8M urea and 0.5×TBE). The gel is preheated and run under 1× TBE (90 mM Tris-borate pH 8.3, 2 mM EDTA) at constant power of 70 W for 2–3 hrs. The gel is dried and autoradiographed overnight at room temperature.

Primer Sets For Hot Multiplex PCR

Due to the two dimensional illustration capacity of autoradiography, blank spaces should be available between markers to avoid overlapping between allelic fragments. Three sets of multiplex were designed to amplify all seven markers. Here, the first dimension is the migration interval; the second dimension is the density of the bands.

Best results were obtained with the primer sets listed below. Other combinations of primers may also be used for multiplex PCR. High background and low or no signal are obtained when Sextolet 150 primer and Sextolet 75-5'primer are included in the same reaction mixture.

TABLE 4

| Primers Name | Primer sequence 5'-3' | $^{32}$P labeled primers | Non labeled primers |
| --- | --- | --- | --- |
| PENTAPlex | | | |
| Sextolet 900E | ATGCGTTTTGGATGAAATGAGATG (SEQ ID NO:16) | 0.05 µm | 0.05 µM |
| Sextolet 180F | CCGGCGGCCGGGGCCCTGCTTCTTAATTTATGGACTATCT (SEQ ID NO:12) | 0.2 µM | 0.2 µM |
| Sextolet 150 | GTACTTATCAGAAACATTTGTTTC (SEQ ID NO:10) | 0.2 µM | 0.2 µM |
| Sextolet 110BS | CCGCCGCGCATTTAGGATGGTGGATTTAC (SEQ ID NO:9) | 0.2 µM | 0.2 µM |
| Sextolet 100C | GCCGGGCGCCCAAGAGAAGCCGCCAGGAAC (SEQ ID NO:8) | 0.2 µM | 0.2 µM |
| Sextolet Trio 5' | CAGAGCGAGACTCT (SEQ ID NO:5) | — | 0.5 µM |
| Sextolet 110t | GGCCGCCGGAAAAGCCTCTTGGGAAAGTA (SEQ ID NO:6) | — | 0.2 µM |
| QUATROPlex A | | | |
| Sextolet 900E | ATGCGTTTTGGATGAAATGAGATG (SEQ ID NO:16) | 0.05 µM | 0.05 µM |
| Sextolet 700B | ATCTGTCCAGAGACAGACGTCAAT (SEQ ID NO:13) | 0.25 µM | 0.25 µM |
| Sextolet 110BS | CCGCCGCGCATTTAGGATGGTGGATTTAC (SEQ ID NO:9) | 0.1 µM | 0.1 µM |
| Sextolet 100C | GCCGGGCGCCCAAGAGAAGCCGCCAGGAAC (SEQ ID NO:8) | 0.2 µM | 0.2 µM |
| Sextolet Trio 5 | CAGAGCGAGACTCT (SEQ ID NO:5) | — | 0.1 µM |
| Sextolet 110t | GGCCGCCGGAAAAGCCTCTTGGGAAAGTA (SEQ ID NO:6) | — | 0.2 µM |
| Sextolet 75-5' | CAGAGCGAGACTCTGTCA (SEQ ID NO:7) | — | 0.2 µM |
| QUATROPlex B | | | |
| Sextolet 800G | CGGCCGGGGCCCATGCCTGCATTCACACCTCTTCCAGT (SEQ ID NO:15) | 0.1 µM | 0.05 µM |
| Sextolet 180A | TGCTTCTTAATTTATGGACTATCT (SEQ ID NO:11) | 0.2 µM | 0.2 µM |
| Sextolet 110BS | CCGCCGCGCATTTAGGATGGTGGATTTAC (SEQ ID NO:9) | 0.2 µM | 0.2 µM |
| Sextolet 100C | GCCGGGCGCCCAAGAGAAGCCGCCAGGAAC (SEQ ID NO:8) | 0.2 µM | 0.2 µM |
| Sextolet Trio 5' | CAGAGCGAGACTCT (SEQ ID NO:5) | — | 0.2 µM |
| Sextolet 110t | GGCCGCCGGAAAAGCCTCTTGGGAAAGTA (SEQ ID NO:6) | — | 0.2 µM |
| Sextolet 75-5' | CAGAGCGAGACTCTGTCA (SEQ ID NO:7) | — | 0.1 |

Cold Multiplex PCR

Multiplex PCR

Two µl of DNA sample equivalent to about 4 ng DNA or more are added to a PCR reaction tube. To this DNA sample, 18 µl of pre-mixed PCR reaction cocktail are added. The final PCR reaction mixture consists of the DNA plus 1 unit of Taq DNA polymerase, 0.1 unit of Pwo DNA polymerase (from Boehringer Manheim Cat. No. 1644 947), and primers (listed below) in 10 mM Tris-HC1, pH 9.0, 50 mM KCl, 2.0 MgCl$_2$, 4% formamide, 0.01% gelatin, 0.2 mM each of four dNTPs. The reaction was carried out with 35 cycles at 94° C. for 45 sec., 52° C. for 60 sec., and 72° C. for 60 sec.

Gel Electrophoresis

Two µl of each multiplex PCR mixture are mixed with 20.5 µl 100% formamide containing 0.5 µl of GS500 (available at PE-ABI Cat. No. 401733). After mixing, the sample is heated at 94° C. for 4 min. and then cooled to 4–6° C. Samples are loaded on the GA310. Electrophoresis is performed using POP6 (PE-ABI) in a 47 cm capillary-microcolumn. The migration module for POP6 was set on filter C and other parameters are as follows:

| Injection Time | 5 sec. |
|---|---|
| Injection Voltage | 15.0 Kv. |

We used three dyes to distinguish between all seven individual markers; green (the fluorescent dye is TET), blue (6-FAM) and yellow (HEX)). The red color (TAMRA) available for the GA310 is used to detect size standards (GENSCAN 500). The allelic fragment of each markers is identified according to its size.

Best results have been obtained with the primer sets listed in Table 5. Other combinations of primer sets may also be used in multiplex PCR.

TABLE 5

| Primers Name | Primer sequence 5'-3' | Labeled primers | Non labeled primers |
|---|---|---|---|
| M1 | | | |
| Sextolet 900E | ATGCGTTTTGGATGAAATGAGATG (SEQ ID NO:16) | (6-FAM) 0.05 μM | 0.05 μM |
| Sextolet 180A | TGCTTCTTAATTTATGGACTATCT (SEQ ID NO:11) | (TET) 0.08 μM | 0.08 μM |
| Sextolet 150 | GTACTTATCAGAAACATTTGTTTC (SEQ ID NO:10) | (6-FAM) 0.4 μM | 0.4 μM |
| Sextolet 110BS | CCGCCGCGCATTTAGGATGGTGGATTTAC (SEQ ID NO:9) | (TET) 0.2 μM | 0.2 μM |
| Sextolet 100C | GCCGGGCGCCCAAGAGAAGCCGCCAGGAAC (SEQ ID NO:8) | (6-FAM) 0.1 μM | 0.1 μM |
| Sextolet Trio 5 | CAGAGCGAGACTCT (SEQ ID NO:5) | — | 0.4 μM |
| Sextolet 110t | GGCCGCCGGAAAAGCCTCTTGGGAAAGTA (SEQ ID NO:6) | — | 0.1 μM |
| M2 | | | |
| Sextolet 800G | CGGCCGGGGCCCATGCCTGCATTCACACCTCTTCCAGT (SEQ ID NO:15) | (HEX) 0.2 μM | 0.2 μM |
| Sextolet 700E | GCCTCAAGAGTGTCCAAACTGAGAC (SEQ ID NO:14) | (TET) 0.1 μM | 0.1 μM |
| Sextolet 75-5' | CAGAGCGAGACTCTGTCA (SEQ ID NO:7) | — | 0.3 μM |
| M3 | | | |
| Sextolet 900E | ATGCGTTTTGGATGAAATGAGATG (SEQ ID NO:16) | (6-FAM) 0.05 μM | 0.05 μM |
| Sextolet 800G | CGGCCGGGGCCCATGCCTGCATTCACACCTCTTCCAGT (SEQ ID NO:15) | (HEX) 0.2 μM | 0.2 μM |
| Sextolet 700E | GCCTCAAGAGTGTCCAAACTGAGAC (SEQ ID NO:14) | (TET) 0.1 μM | 0.1 μM |
| Sextolet 180A | TGCTTCTTAATTTATGGACTATCT (SEQ ID NO:11) | (TET) 0.06 μM | 0.06 μM |
| Sextolet 110BS | CCGCCGCGCATTTAGGATGGTGGATTTAC (SEQ ID NO:9) | (TET) 0.3 μM | 0.3 μM |
| Sextolet 100C | GCCGGGCGCCCAAGAGAAGCCGCCAGGAAC (SEQ ID NO:8) | (6-FAM) 0.07 μM | 0.07 μM |
| Sextolet Trio 5 | CAGAGCGAGACTCT (SEQ ID NO:5) | — | 0.4 μM |
| Sextolet 110t | GGCCGCCGGAAAAGCCTCTTGGGAAAGTA (SEQ ID NO:6) | — | 0.2 μM |
| Sextolet 75-5' | CAGAGCGAGACTCTGTCA (SEQ ID NO:7) | — | 0.3 μM |

-continued

| Collection Time | 50 min. |
|---|---|
| EP Voltage | 15.0 Kv. |
| Heatplate Temperature | 50° C. |
| Syringe Pump Time | 120 sec. |
| Pre Injection EP | 300 sec. |

Primer Sets For Cold Multiplex PCR

Due to the three dimensional illustration capacity of GA310, overlapping allelic fragments can be distinguished from each other. Here, the first dimension is the migration interval; the second dimension is the peak height of each allelic fragment and the third dimension is the color indicating the specific markers. Principally, many markers can be amplified with one multiplex PCR and analyzed in a single run. Since the Sextolet 150 and Sextolet 75-5' cannot be included in the same amplification mix, two separate PCR are necessary to amplify all seven Markers (M1 and M2). However, only one multiplex PCR is necessary if all the markers except Sextolet 150 are simultaneously amplified (M3).

The present invention will be more readily understood by referring to the following examples which are given to illustrate the invention rather than to limit its scope.

EXAMPLE I

Paternity Testing

When the method of the present invention is used to identify the biological father of a child, the DNA from this person is amplified by the method of the present invention and the DNA profile of the father, using the PENTAPlex, or QUATROPlex A or QUATROPlex B or combined M1 and M2, or using the M3 multiplex set, is compared with that of the child. If the mother's DNA is available, the mean paternity index (PI) of PENTAPlex is 184, leading to a probability of paternity 99.46%. The mean PI for QUATROPlex A is 388 leading to a probability of paternity 99.74%. The mean PI for QUATROPlex B is 55, leading to a probability of paternity 98.21%. The mean PI for combined M1 and M2 is 4255, leading to a probability of paternity 99.98%. If M3 is used in this testing procedure, the mean paternity index (PI) is 2616, leading to a probability of paternity 99.96%.

EXAMPLE II

DNA Fingerprinting

When the method of the present invention is used to identify whether two biological samples refer to the same individual, the above mentioned method could be employed and the comparison of the allelic profiles from the two samples made. Whether from different or from the same individual, the DNA samples are more likely to be matched or refuted using the present invention than with any other DNA matching system currently available. If the PENTA-Plex multiplex set is used, a possible identical DNA profile is expected to be found in every $9.9 \times 10^6$ individual. The matching probability is $1.9 \times 10^7$ with QUATROPlex A and $1.6 \times 10^5$ with QUATROPlex B. With M3, the matching probability is $2.5 \times 10^{10}$. When combined, M1 and M2 will reach a matching probability of $1.5 \times 10^{11}$.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A STR marker for DNA fingerprinting of a DNA sample, consisting of an isolated polynucleotide consisting of the sequence selected from the group consisting of SEQ ID NO:18, SEQ ID NO:19, SEQ ID NO:20, SEQ ID NO:21 and SEQ ID NO:22, and complementary sequences thereto.

2. The STR marker of claim 1, wherein said DNA sample is from a human being.

3. A DNA amplification primer pair for the amplification of at least one STR marker, which comprises a pair of 5' and 3' primers selected from the group consisting of SEQ ID NO:5 and SEQ ID NO:8 ; SEQ ID NO:6 and SEQ ID NO:9; SEQ ID NO:5 and SEQ ID NO:10; SEQ ID NO:5 and SEQ ID NO:11; SEQ ID NO:5 and SEQ ID NO:12; SEQ ID NO:7 and SEQ ID NO:13; SEQ ID NO:7 and SEQ ID NO:14; SEQ ID NO:7 and SEQ ID NO:15; and SEQ ID NO:5 and SEQ ID NO:16

4. A method for the DNA fingerprinting identification of genetically related or unrelated individuals, which comprises the steps of:

a) collecting genomic DNA sample of said individuals;

b) performing DNA amplification of said DNA sample of step a) using a primer pair as defined in claim 3; and c) separating said amplified DNA from said DNA sample of step b), whereby seven markers of said genomic DNA of different size are amplified and serve as DNA fingerprinting of said individuals.

5. The method of claim 4, wherein said DNA amplification of step b) is effected by PCR or by asymmetric PCR procedure.

6. The method of claim 4, wherein said DNA separation of step c) is effected using an automated genetic analyzer or a gel electrophoresis procedure.

7. The method of claim 6, wherein said gel electrophoresis procedure is a urea-PAG separation method.

8. A method for the DNA fingerprinting identification of human DNA samples, which comprises the steps of:

a) performing DNA amplification of said DNA samples using a primer pair as defined in claim 3; and b) separating said amplified DNA from said DNA sample of step a), whereby seven markers of said genomic DNA of different size are amplified and serve as DNA fingerprinting of said DNA samples.

9. The method of claim 8, wherein said DNA fingerprinting of said DNA samples is for verifying transplanted tissues in research or therapeutic procedures.

10. The method of claim 8, wherein said DNA fingerprinting of said DNA samples is for single cell genetic profiling in research or therapeutic procedure.

11. The method of claim 8, wherein said DNA fingerprinting of said DNA samples is for verifying sample mix-up or contamination.

12. The method of claim 8, wherein said DNA fingerprinting of said DNA samples is for testing, establishing or verifying paternity, maternity or consanguinity of individuals.

13. A kit for simultaneous amplification of STR markers, which comprises:

a) a primer pair as defined in claim 3; and b) a STR marker as defined in claim 1.

* * * * *

```
                              SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
            (A) LENGTH: 5 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:1:

AAAAC                                                                          5

(2) INFORMATION FOR SEQ ID NO:2:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:2:

AAAGGAAGAA AG                                                                 12

(2) INFORMATION FOR SEQ ID NO:3:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:3:

AAAGAGAAAG                                                                   10

(2) INFORMATION FOR SEQ ID NO:4:

(i) SEQUENCE CHARACTERISTICS:
            (A) LENGTH: 11 base pairs
            (B) TYPE: nucleic acid
            (C) STRANDEDNESS: single
```

```
            (D) TOPOLOGY: linear (ii) MOLECULE TYPE: DNA (xi) SEQUENCE DESCRIPTION: SEQ ID NO:4:

AAAGAGAAAG G                                                              11

(2) INFORMATION FOR SEQ ID NO:5:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:5:

CAGAGCGAGA CTCT                                                           14

(2) INFORMATION FOR SEQ ID NO:6:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:6:

GGCCGCCGGA AAAGCCTCTT GGGAAAGTA                                           29

(2) INFORMATION FOR SEQ ID NO:7:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:7:

CAGAGCGAGA CTCTGTCA                                                       18

(2) INFORMATION FOR SEQ ID NO:8:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:8:

GCCGGGCGCC CAAGAGAAGC CGCCAGGAAC                                          30

(2) INFORMATION FOR SEQ ID NO:9:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: oligonucleotide
```

(xi) SEQUENCE DESCRIPTION: SEQ ID NO:9:

CCGCCGCGCA TTTAGGATGG TGGATTTAC                                        29

(2) INFORMATION FOR SEQ ID NO:10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:10:

GTACTTATCA GAAACATTTG TTTC                                             24

(2) INFORMATION FOR SEQ ID NO:11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:11:

TGCTTCTTAA TTTATGGACT ATCT                                             24

(2) INFORMATION FOR SEQ ID NO:12:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:12:

CCGGCGGCCG GGGCCCTGCT TCTTAATTTA TGGACTATCT                             40

(2) INFORMATION FOR SEQ ID NO:13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:13:

ATCTGTCCAG AGACAGACGT CAAT                                             24

(2) INFORMATION FOR SEQ ID NO:14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:14:

GCCTCAAGAG TGTCCAAACT GAGAC                                            25

(2) INFORMATION FOR SEQ ID NO:15:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:15:

```
CGGCCGGGGC CCATGCCTGC ATTCACACCT CTTCCAGT                        38
```

(2) INFORMATION FOR SEQ ID NO:16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:16:

```
ATGCGTTTTG GATGAAATGA GATG                                       24
```

(2) INFORMATION FOR SEQ ID NO:17:

(i) SEQUENCE CHARACTERISTICS:
        (A) LENGTH: 1013 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:17:

```
AAAGGCAGGA TAAATGTTTG ACTTTTTTCC TTTTATTTGC CACTTTTCAA AACAAGTATC   60
ATAATAAACT CACTAATTTA AACATTTTGA TGTATTTTAA TACAGGGTAG TTATTGTTCT  120
TATTGATGCT TAAATTATCC ATCTTTGACC AATGGGAGCC TAGTTATTTT GGTTCCCTTG  180
ACATTTTGAC AGAAATCCAA CGATCTTTCG ATCAATGTTT GGTAGTTTCC TTGTTTCTAG  240
TTTATTTTGT ACTTTTTCTT CTCCTGGTTT TAGAATTAGC CTTTTTCCTA AGGATACTCA  300
GTTTTTTTTT TTGACACAGT TATACATGAT GTTTTATAGG TTAACTATGA TAGAAAAAGC  360
CTTGATAGGC TTCTTTGTTA GAAAGGAAAG GCCAAATATT TCCAGGAATA TTGGAGGTTC  420
AGTTCCTTGG CACAGATAGG TGGTTTTCTC TGAAATTAAT TTGGAAAATT CTATCAGGTG  480
AGAGCATATC ATTGTTGTGT TTGTAAAAAA CAATGGCCAA TAGAGATAAC AGTTTATGAA  540
AAACCACTGT TTTCTATAAT GAAGAAGAAG ACATCTTATC TTTGTAAACA AAGGAGCAAA  600
GGAAAGTGTG ATTTCAGAAC TGCTTGGTTC TATGTACTGG AGATTCAGAT GTGGGGAGGC  660
ACTCAGAAGT GTGACTTTTG GTCTCAGCCC TGTTTGGAGC CCTTAGCCCT AAGTCAGAGA  720
ATGTACACAA TCTACCTGGG GAGGCTGAGC TGCCCACTGG GAACAGAGGT TCTTGGGTGT  780
TCCACTGCTC CCAAGTCAGA ATCCTGGGTC TCCTACTAAT ACCTGGGCAG TTCACTTTTC  840
TCAGGTCTCT TTTCTTTTCT AGCAGAGCCT AGAGCAGAGT AACTACTTCA GAATGCGTTT  900
TGGATGAAAT GAGATGACCA CATGAGACAG CAACAACTTG TGCTCAGCTT GGGCCCCTTC  960
TTTCTTTCCT TTCTCTTTTC TTTCCTTCTT TCCTTCTTTA GAGTCTCGCT CTG        1013
```

(2) INFORMATION FOR SEQ ID NO:18:

(i) SEQUENCE CHARACTERISTICS:
     (A) LENGTH: 139 base pairs
     (B) TYPE: nucleic acid
     (C) STRANDEDNESS: double
     (D) TOPOLOGY: linear (ii) MOLECULE TYPE: Genomic DNA (xi) SEQUENCE DESCRIPTION: SEQ ID NO:18:

```
TTTCCAGCTG GAACGAAGAC CCAGCCACAT GCCTGCATTC ACACCTCTTC CAGTCTCTTT      60

CCTTCTTTCT TTTTCTTTCT CTTTCCTTCT TTCCTCCCTT TCTTTTTTCT TTCTTTCTTT     120

CTGACAGAGT CTCGCTCTG                                                  139
```

(2) INFORMATION FOR SEQ ID NO:19:

(i) SEQUENCE CHARACTERISTICS:
          (A) LENGTH: 502 base pairs
          (B) TYPE: nucleic acid
          (C) STRANDEDNESS: double
          (D) TOPOLOGY: linear (ii) MOLECULE TYPE: Genomic DNA (xi) SEQUENCE DESCRIPTION: SEQ ID NO:19:

```
AAGACCCAGC CACATGCCTG CATTGACATA CACATAAGCA GTCACCAAGA CACAATCCAA      60

CTGCAGCAGT GATCAACAAG CCCCAAGAGT GACCAGACTG AGTCAGGGTG CTTTCCTCTC     120

TCAGCTGCTT GGCTTGTTCA ATCTCAAATG GAAATTCCTT CAGAATTCCC CAAATCAAGA     180

GGAGCGGTTC CTGCTTTTTG GACTCACAGA AGACACTCAC TTGTCCAGAT GCAGATGTGC     240

ACATACAGAC ACAAATAAGC AATTATTAAC AAGCCTCAAG AGTGTCCAAA CTGAGACAGG     300

GAGCTTTCCT CTCTTCATTG GTTAGGCTTG TTCAACCTGC AAATAGATTC CTCAAATCTA     360

GAGGAGCCAT ATTTGCTGTC AGCTACCCAC AAAAGACACT TATCTGTCCA GAGACAGACG     420

TCAATTTTTT CTTTCTTCCT TTTCTTTCTT CTTTCTCTTT CTTCTTTCTT TTTTTTTTT      480

TTTTTGACAG AGTCTCGCTC TG                                              502
```

(2) INFORMATION FOR SEQ ID NO:20:

(i) SEQUENCE CHARACTERISTICS:
          (A) LENGTH: 195 base pairs
          (B) TYPE: nucleic acid
          (C) STRANDEDNESS: double
          (D) TOPOLOGY: linear (ii) MOLECULE TYPE: Genomic DNA (xi) SEQUENCE DESCRIPTION: SEQ ID NO:20:

```
TTTGTTTCTA AGCATTTGTG TTTATAAATG AATACATGTA AAATATATTT TTGCTTCTTA      60

ATTTATGGAC TATCTTCTGA TTTCCCTTCA TTTTTTAATA GCTGTTTTA ACCTGAGAAT     120

TCTATCTAGC CCAACTGAAA TTATTACTTG TTTTATTTTA TGTATTTGTT TATTTGAGAT     180

AGAGTCTCGC TCTGA                                                     195
```

(2) INFORMATION FOR SEQ ID NO:21:

(i) SEQUENCE CHARACTERISTICS:
          (A) LENGTH: 134 base pairs
          (B) TYPE: nucleic acid
          (C) STRANDEDNESS: double
          (D) TOPOLOGY: linear (ii) MOLECULE TYPE: Genomic DNA -continued (xi) SEQUENCE DESCRIPTION: SEQ ID NO:21:

TCTAAAGTAC TTATCAGAAA CATTTGTTTC TTTTTAAAAA AAAATTTTTG TTTCTTTTTT    60

AAAAAAATAT TTTGTATTGT TTAGTTTTTG CAGAGATGGA CGGTCATCAT GTTTTGTTTG    120

AGAGTCTCGC TCTG    134

(2) INFORMATION FOR SEQ ID NO:22:

(i) SEQUENCE CHARACTERISTICS:
        (A) LENGTH: 114 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:22:

AGCCACATGC CTGCATTCAC AAGTAAGAAG GAAAAGCCTC TTGGGAAAGT AAGTCTTTGT    60

TTTTATTGGT TTTTGTTTTG CACAGAAGCC ACGTAAATCC ACCATCCTAA ATAA    114

(2) INFORMATION FOR SEQ ID NO:23:

(i) SEQUENCE CHARACTERISTICS:
        (A) LENGTH: 91 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:23:

CAGAGCGAGA CTCTGTCAAT AAATAAACAA ACAAAAACTC TGGTTCCTGG CGGCTTCTCT    60

TGAAATATCA GAATGGTACC ACTGGGTAAC C    91